United States Patent [19]

Scherm et al.

[11] E Patent Number: Re. 32,581

[45] Reissued Date of Patent: Jan. 19, 1988

[54] CERTAIN SUBSTITUTED PHENYL ESTERS OF NICOTINIC ACID, COMPOSITIONS AND METHODS OF USING SAME FOR TREATMENT OF HYPERLIPIDEMIA

[75] Inventors: Arthur Scherm, Bad Homburg; Dezsoe Peteri, Hattersheim; Klaus Hummel, Frankfurt, all of Fed. Rep. of Germany

[73] Assignee: Merz + Co. GmbH & Co., Frankfurt am Main, Fed. Rep. of Germany

[21] Appl. No.: 634,472

[22] Filed: Jul. 24, 1984

Related U.S. Patent Documents

Reissue of:

[64] Patent No.: 4,321,268
Issued: Mar. 23, 1982
Appl. No.: 222,679
Filed: Jan. 5, 1981

U.S. Applications:

[63] Continuation-in-part of Ser. No. 119,576, Feb. 7, 1980, abandoned.

[30] Foreign Application Priority Data

Feb. 8, 1979 [DE] Fed. Rep. of Germany ..... 2904757

Feb. 8, 1979 [DE] Fed. Rep. of Germany ..... 3009099

[51] Int. Cl.[4] ..... C07D 213/55; A61K 31/455

[52] U.S. Cl. ..... 514/356; 546/285; 546/322

[58] Field of Search ..... 546/322, 285; 514/356

[56] References Cited

U.S. PATENT DOCUMENTS 3,933,835 1/1976 Haas et al. ..... 546/285

OTHER PUBLICATIONS

Fiedler, Chem. Abs., vol. 63, (9), 11486d, Oct. 25, 1965.

Fiedler article, Die Pharmazie, vol. 20(7), pp. 401–404 (1965).

Zinner et al., Archive der Pharmazie 291, pp. 330–338 (1958).

*Primary Examiner*—Alan L. Rotman

*Attorney, Agent, or Firm*—Gordon W. Hueschen

[57] ABSTRACT

Novel hypolipidemic nicotinates and related esters, being phenoxy organic compounds, are disclosed, as well as pharmaceutical compositions thereof and method of treating hyperlipidemia therewith.

12 Claims, No Drawings

CERTAIN SUBSTITUTED PHENYL ESTERS OF NICOTINIC ACID, COMPOSITIONS AND METHODS OF USING SAME FOR TREATMENT OF HYPERLIPIDEMIA

Matter enclosed in heavy brackets [ ] appears in the original patent but forms no part of this reissue specification; matter printed in italics indicates the additions made by reissue.

This application is a continuation-in-part of our prior-filed copending application Ser. No. 119,576, filed Feb. 7, 1980 and subsequently abandoned.

The invention relates to new pharmaceutically effective compounds and their pharmaceutically applicable salts formed with organic or inorganic acids as well as to a process for the manufacture of these compounds.

It is known that atherosclerosis is caused by the accumulation of lipids in the aorta and the coronary, cerebral and peripheral arteries. This results in an increased risk of thromboses or artery obstruction. Dependent on the nature of the increased plasma protein level, either the elevated cholesterol or triglyceride level is of importance. In this connection even cholesterol levels exceeding 200–300 mg/100 ml serum and triglyceride levels of 45–66 mg/100 ml serum are considered to be extremely elevated.

The two most widely known classes of active substances used in the treatment of hyperlipidemias comprise the ethyl ester of 2-(p-chlorophenoxy)-isobutyric acid—known as clofibrate—and its salts as well as nicotinic acid which influence the serum lipids by different modes of action. While in test animals doses of 30–500 mg/kg body weight mainly effect a lowering of the cholesterol level in addition to a slight reduction of the free fatty acids, 3-pyridyl carbinol, nicotinic acid and its salts bring about a great reduction of the free fatty acids already at a low dosage between 0.5 and 30 mg/kg body weight. None of the substances has, however, a significant reducing influence on triglycerides. Besides that, due to its unpleasant and known side effects (flush, headache, nausea, vomiting) nicotinic acid can only be conditionally used so that therapy often has to be discontinued prematurely.

Additionally, it is known that clofibrate, in fact, effects a fall of the initial values of triglycerides (TG) and pre-$\beta$-lipoproteins by up to 50%, this degree of lowering not being achieved in the case of cholesterol. In about 20% of the cases the cholesterol (CH) in the $\beta$- and $\alpha$-lipoproteins is even further increased. Nicotinic acid and its derivatives, on the contrary, act predominantly on elevated cholesterol values and free fatty acids, whereas the decrease of the endogenous resynthesis of the triglycerides via inhibition of tissue lipolysis is only a secondary effect (cf. Verhandlungen der Deutschen Gesellschaft für innere Medizin, 82. Kongress, gehalten zu Wiesbaden vom 25. bis 29.4.1976, Teil I, J. F. Bergmann Verlag München).

Moreover, FR-PS 6975 mentions the 3-pyridyl carbinol ester of clofibric acid as effective lipid- and cholesterol-lowering component. This compound, although being predominantly used in the form of the nicotinate, can only be administered in low dosage due to the high portion of its pyridine component and the thus resulting side effects. It is, therefore, of only little therapeutic benefit.

All the aforementioned substances effect a significant reduction of only one of the lipid components, e.g., the triglycerides, while the other lipid components are therapeutically not or only slightly influenced. This therapeutic effect can only be achieved by a dose increase.

Therefore, the objective was to find other compounds having a lowering effect on several lipid components but without dose increase.

Unexpectedly, this requirement is met by the claimed new compounds having the general formula explained in claim 1. The compounds according to the invention exhibit a strong effect on both increased serum triglyceride and cholesterol values. In comparison with nicotinic acid and the ethyl ester of 2-(p-chlorophenoxy)isobutyric acid the dosages are incomparably lower so that possible side effects are reduced to minimum.

The new compounds are solid substances.

In the following the manufacture of the new compounds is described:

EXAMPLE 1

Preparation of p-cyclohexylphenyl nicotinate 17.6 g (100 mmol) of cyclohexylphenol and 19 g (106 mmol) of nicotinic acid chloride hydrochloride was mixed with 250 ml of dry pyridine and kept at 40° C. for 4 hours. Subsequently, the mixture was cooled in the ice bath, and water added in portions. After addition of 10 ml of water a clear solution was obtained. Water (50 ml) was admixed until strong turbidity appeared. After stirring the mixture for a longer period of time the product crystallized in the ice bath. The precipitate was sucked off, freed from pyridine by washing with water and dried. A second fraction was obtained from the filtrate by further adding water (60 ml).

Yield: 70% of the theoretical value. mp.: 103° C.

| | Analysis | |
|---|---|---|
| | calculated | found |
| C | 76.86 | 76.83 |
| H | 6.76 | 6.76 |
| N | 4.98 | 5.05 |

EXAMPLE 2

Preparation of p-(1-adamantylphenyl)-nicotinate 11.4 g (50 mmol) of p-1-adamantylphenol and 10 g (56 mmol) of nicotinic acid chloride hydrochloride was mixed with 150 ml of dry pyridine and kept at 45° C. for 4 hours. By adding 40 ml of water and stirring in the ice bath the product formed a precipitate which was sucked off, washed with water and dried.

Yield: 78% of the theoretical value. mp.: 199° C.

| | Analysis | |
|---|---|---|
| | calculated | found |
| C | 79.27 | 78.01 |
| H | 6.90 | 6.82 |
| N | 4.20 | 4.50 |

EXAMPLE 3

Preparation of 2-(p-chlorophenoxy)-isobutyric acid-p-(1-adamantylacetyl)-phenyl ester 6.75 g (25 mmol) of p-(1-adamantylacetyl)-phenol and 6 g (25.7 mmol) of 2-(p-chlorophenoxy)-isobutyric acid chloride was mixed with 60 ml of dry pyridine and kept at 40° C. for 4 hours. After addition of 40 ml of water a crystalline product was obtained which was sucked off, washed with water and dried.

Yield: 77% of the theoretical value. mp.: 114° C.

| | Analysis | |
|---|---|---|
| | calculated | found |
| C | 72.03 | 72.12 |
| H | 6.64 | 6.61 |

EXAMPLE 4

Preparation of p-cyclododecylphenyl nitocinate 8 g (30.8 mmol) of p-cyclododecylphenol and 5.9 g (33.2 mmol) of nicotinic acid chloride hydrochloride was mixed with 140 ml of dry pyridine and kept at 30° C. for 15 hours. Subsequently, 42 ml of water was added slowly drop by drop, and the mixture cooled to 0° C. The crystallized precipitate was sucked off, freed from pyridine by washing with water and dried.

Yield: 85% of the theoretical value. mp.: 98° C.

| | Analysis | |
|---|---|---|
| | calculated | found |
| C | 78.91 | 79.01 |
| H | 8.50 | 8.54 |

EXAMPLE 5

Preparation of p-(cyclohexylacetyl)-phenyl nicotinate 11 g (50 mmol) of p-cyclohexylacetylphenol and 9.6 g (54 mmol) of nicotinic acid chloride hydrochloride was mixed with 160 ml of dry pyridine and stirred for 8 hours at 40° C. Subsequently, water (66 ml) was added drop by drop until the solution was turbid. The solution was placed in the ice bath, the precipitate sucked off, freed from pyridine by washing with water and dried.

Yield: 55% of the theoretical value. mp.: 103° C.

| | Analysis | |
|---|---|---|
| | calculated | found |
| C | 74.30 | 74.07 |
| H | 6.50 | 6.51 |

EXAMPLE 6

Preparation of o-cyclohexylphenyl nicotinate hydrochloride 15 g (85 mmol) of o-cyclohexylphenol and 16.5 g (93 mmol) of nicotinic acid chloride hydrochloride was mixed with 200 ml of dry pyridine and stirred for 24 hours at 30° C. After cooling precipitated pyridine hydrochloride was sucked off and 300 ml of water added. The precipitated raw product was washed with two 200 ml portions of water, dissolved in alcohol and reduced by means of a rotary evaporator. The remaining viscous oil was dissolved in 500 ml of dry ether and hydrochlorinated with HCl gas. Subsequently, the mixture was filtered, washed with ether and dried.

Yield: 52% of the theoretical value. mp.: 151°-2° C.

| | Analysis | |
|---|---|---|
| | calculated | found |
| C | 68.03 | 68.11 |
| H | 6.29 | 6.30 |
| Cl | 11.18 | 11.20 |

EXAMPLE 7

Preparation of 5,6,7,8-Tetrahydro-1-naphthyl-nicotinate 7 g (47 mmol) of 5,6,7,8-tetrahydro-1-naphthol and 9 g (50 mmol) of nicotinic acid chloride hydrochloride was mixed with 130 ml of dry pyridine and stirred for 24 hours at 30° C. After cooling precipitated pyridine hydrochloride was sucked off, and the filtrate mixed with 300 ml of water. The precipitated raw product was washed with two 200 ml portions of water and recrystallized from methanol.

Yield: 65% of the theoretical value. mp.: 86° C.

| | Analysis | |
|---|---|---|
| | calculated | found |
| C | 75.88 | 75.81 |
| H | 5.93 | 6.07 |

EXAMPLE 8

Preparation of 2-t-butyl-4-cyclohexylphenyl nicotinate 12 g (52 mmol) of 2-t-butyl-4-cyclohexylphenol and 10 g (56 mmol) of nicotinic acid chloride hydrochloride was mixed with 150 ml of dry pyridine and stirred for 48 hours at 35° C. After cooling precipitated pyridine hydrochloride was sucked off and the filtrate mixed with 75 ml of water. The precipitated raw product was freed from pyridine by washing with water and recrystallized from alcohol.

Yield: 73% of the theoretical value. mp.: 115° C.

| | Analysis | |
|---|---|---|
| | calculated | found |
| C | 78.33 | 78.03 |
| H | 8.01 | 7.88 |
| N | 4.15 | 4.07 |

EXAMPLE 9

Preparation of p-cumylphenyl nicotinate 42.4 g (200 mmol) of p-cumylphenol and 40 g (220 mmol) nicotinic acid chloride hydrochloride was mixed with 600 ml dry pyridine and stirred for 24 hours at 40° C. After cooling precipitated pyridine hydrochloride was sucked off and the filtrate mixed with 150 ml of water. The precipitated raw product was washed with two 100 ml portions of water and recrystallized from methanol.

Yield: 70% of the theoretical value. mp.: 56° C.

| | Analysis | |
|---|---|---|
| | calculated | found |
| C | 79.49 | 79.59 |
| H | 5.99 | 6.06 |

EXAMPLE 10

Preparation of p-chlorobenzoylphenyl nicotinate 15 g (64.5 mmol) of p-chlorobenzoylphenol and 12 g (68 mmol) of nicotinic acid chloride hydrochloride was mixed with 200 ml dry pyridine and stirred for 24 hours at 40° C. After cooling 200 ml water were added and the precipitated product washed twice with 80 ml of water and recrystallized from methanol.

Yield: 80% of the theoretical value. mp.: 172° C.

| | Analysis | |
|---|---|---|
| | calculated | found |
| C | 67.55 | 67.41 |
| H | 3.56 | 3.64 |

Toxicity Tests

TABLE 1

| No. of Example* | $R^1$ | $R^2$ | $LD_{50}$ Rat (mg/kg) | $ED_{50}$ Rat (mg/kg) | Therap. Index |
|---|---|---|---|---|---|
| 2 | 1-Adamantyl | H | 3200 | 68 | 47 |
| 1 | Cyclohexyl | H | 2200 | 50 | 44 |
| 8 | Cyclohexyl | 2-tert.-Butyl | 1700 | 30 | 56 |
| 6 | H | 2-Cyclohexyl | 2050 | 22 | 93 |
| 2-p-Chlorophenoxy isobutyric acid ethyl ester (standard) | | | 1500 | ca. 300 | 5 |
| Nicotinic acid (standard) | | | 4000 | ca. 500 | 8 |

*$R^3$ in each of Examples 1, 2, 6, and 8 is pyridinoyl-(3)

Table 1 shows that the toxicity values are in a comparable range thus resulting in excellent values for the therapeutic index.

Evidence of effectiveness

Additionally, experiments on female Wistar rats were carried out. For a period of 3 weeks the animals received a special diet with a very high fat content. Starting from the second week, half the rats were treated with a dosage of 100 and 25 mg/kg body weight. After the third week blood samples were taken 18 hours after administration of the last dose. Triglyceride and cholesterol concentrations were compared with that of the untreated animals. Cholesterol and triglycerides were determined with the aid of the Boehringer enzymatic test. As summarized in Table 2, highly significant reductions of both parameters were achieved. Table 2 also shows that the separate administration of clofibrate and nicotinic acid was by far less effective.

TABLE 2

| No. of compound** (Example) | $R^1$ | $R^2$ | Dosage Rat (mg/kg) | Chol. Red in % | Tri-glyc. Red in % |
|---|---|---|---|---|---|
| 2 | 1-Adamantyl | H | 100 | 28 | 47 |
| 1 | Cyclohexyl | H | 100 | 45 | 19 |
| 8 | Cyclohexyl | 2-tert.Butyl | 25 | 9 | 8 |
| 9 | Cumyl | H | 100 | 24 | 1 |
| 6 | H | 2-Cyclohexyl | 25 | 18 | 16 |
| 7 | H | $(-CH_2-)_n$* n = 4 | 100 | 22 | 18 |
| 3 | 1-Adamantyl-acetyl | H | 100 | 27 | 35 |
| 10 | p-Chlorobenzoyl | H | 100 | 29 | — |
| | Nicotinic acid (standard) | | 100 | 7 | — |
| | 2-p-Chlorophenoxy-isobutyric acid ethyl ester (standard) | | 100 | — | 8 |

*Compound No. 7 according to the invention, wherein $R^2 = (-CH_2-)_n$ and n = 4, forms a cyclic ring thus leading to the compound with tetraline structure described in Example 7.
**$R^3$ in all of the compounds except compound No. 3 is pyridinoyl-(3). For compound No. 3 $R^3$ is 2-methyl-2-(p-chloro phenoxy)propionyl.

Subject matter of the invention are therefore new compounds of the general formula:

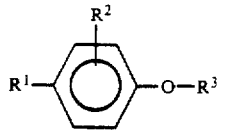

Wherein $R^1$ =

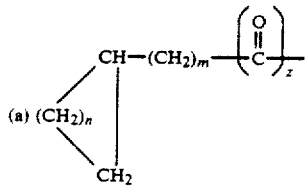

where n = 3–12
m = 0–1
z = 0–1

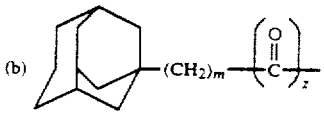

where m = 0–1
and z = 0–1

(c) Cumyl
(d) p-Chlorobenzoyl
(e) 1-Piperidinyl
(f) 2-Pyrimidinyl
(g) Hydrogen, but $R^1$ can only equal hydrogen when $R^2$ equals Cycloalkyl or Cycloalkylene $(-CH_2-)_n$ and $R^2$ =
(a) $(-CH_2-)_n$, where n = 0 or 4
(b) Halogen
(c) $C_1$–$C_6$—Alkyl or cycloalkyl
(d) Methoxy
(e) Ethoxy
(f) Trifluoromethyl
(g) Nitro
(h) hydrogen, -continued and $R^3$ =

(a) 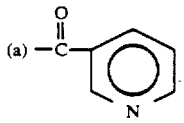

(b) 2-Methyl-2-(p-chlorophenoxy)-propionyl and their pharmaceutically applicable salts formed with organic or inorganic acids.

Additionally, the invention relates to a process for the manufacture of the compounds according to claim 1, characterized in that known esterification methods are used such as, e.g., the reaction of 1 mol and nicotinic acid chloride with 1 mol of starting phenol in the presence of at least 1 mol of an acid-binding substance, e.g, pyridine. The preparations according to the invention consist of compounds according to claim 1 and usual pharmaceutical adjuvants.

The compounds according to the invention may be processed into pharmaceutical agents containing a carrier or a diluent in addition to the active substance. They can be administered by the oral and the parenteral route.

Solid preparations for oral administration are capsules, tablets, pills, powders, granulates. In such solid preparations the active substance is mixed with at least one inert diluent such as cane sugar, lactose or starch. Additional substances may be added such as lubricants or buffers. The tablets or pills may be subject to enteric-coating.

Liquids for oral application are emulsions, solutions, suspensions containing the commonly used inert diluents such as water. Additionally, such liquid agents may contain wetting, emulsifying and dispersing agents as well as sweetening, flavouring and odorous substances.

Preparations for parenteral application are, among others, sterile, aqueous or non-aqueous solutions, suspensions or emulsions. Substances known for this form of presentation are used as carrier material.

Dependent on mode of application and duration of treatment, the dosage of the active substances in the preparations may vary.

We claim:

[1. Compounds having the general formula:

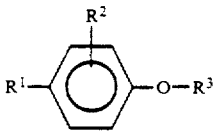

Wherein $R^1$ =

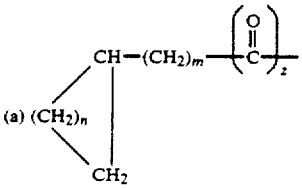

where n = 3–12
m = 0–1
z = 0–1

-continued (b) 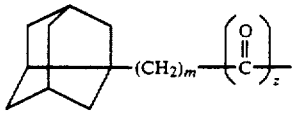

where m = 0–1
and z = 0–1

(c) Cumyl
(d) p-Chlorobenzoyl
(e) Hydrogen, but $R^1$ can only equal hydrogen when $R^2$ equals Cycloalkyl or Cycloalkylene $(-CH_2-)_n$ and $R^2$ =
(a) $(-CH_2-)_n$, where n = 0 or 4
(b) Halogen
(c) $C_1$–$C_6$—Alkyl or $C_3$–$C_6$—cycloalkyl
(d) Methoxy
(e) Ethoxy
(f) Trifluoromethyl
(g) Nitro
(h) hydrogen, and $R^3$ =

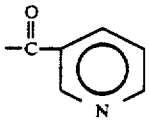

and pharmaceutically-acceptable acid addition salts thereof.]

[2. A compound of claim 1 which is cyclohexylphenylnicotinate or an acid addition salt thereof.]

[3. A compound of claim 1 which is cyclohexylphenylnicotinate.]

[4. A compound of claim 1 which is cyclohexylphenylnicotinate hydrochloride.]

5. A compound of claim [1] *25* which is cyclododecylphenyl-nicotinate.

6. A compound of claim [1] *25* which is 5,6,7,8-tetrahydro-1-naphthyl-nicotinate.

7. A compound of claim [1] *25* which is (1-adamantylphenyl)-nicotinate.

8. A compound of claim [1] *25* which is (cyclohexylacetyl)-phenylnicotinate.

[9. A compound of claim 1 which is p-cyclohexylphenyl nicotinate.]

[10. A compound of claim 1 which is o-cyclohexylphenyl nicotinate hydrochloride.]

[11. A compound of claim 1 which is ortho-cyclohexylphenyl nicotinate, or a pharmaceutically-acceptable acid addition salt thereof.]

12. A compound of claim [1] *25* which is 2-tertiarybutyl-4-cyclohexylphenyl nicotinate, or a pharmaceutically-acceptable acid addition salt thereof.

[13. A pharmaceutical composition useful for the treatment of hyperlipidemia comprising an effective hyperlipidemic dosage of a compound according to claim 1 in admixture together with a pharmaceutically-acceptable carrier or diluent.]

14. A pharmaceutical composition of claim [13] *26*, wherein the active ingredient is 5,6,7,8-tetrahydro-1-naphthyl-nicotinate.

[15. A pharmaceutical composition of claim 13, wherein the active ingredient is p-cyclohexylphenyl nicotinate.]

[16. A pharmaceutical composition of claim 13, wherein the active ingredient is o-cyclohexylphenyl nicotinate hydrochloride.]

[17. A pharmaceutical composition of claim 13, wherein the active ingredient is ortho-cyclohexylphenyl nicotinate, or a pharmaceutically-acceptable acid addition salt thereof.]

18. A pharmaceutical composition of claim [13] *26*, wherein the active ingredient is 2-tertiarybutyl-4-cyclohexylphenyl nicotinate, or a pharmaceutically-acceptable acid addition salt thereof.

[19. Method for the treatment of hyperlipidemia comprising the step of administering to a subject in need of such therapy, by the oral or parenteral route, an effective hyperlipidemic amount of a compound of claim 1.]

20. Method of treating according to claim [19] *27*, wherein the active ingredient is 5,6,7,8-tetrahydro-1-naphthyl-nicotinate.

[21. A method of treating according to claim 19, wherein the active ingredient is p-cyclohexylphenyl nicotinate.]

[22. A method of treating according to claim 19, wherein the active ingredient is o-cyclohexylphenyl nicotinate hydrochloride.]

[23. Method of treating according to claim 19, wherein the active ingredient is ortho-cyclohexylphenyl nicotinate, or a pharmaceutically-acceptable acid addition salt thereof.]

24. Method of treating according to claim [19] *27*, wherein the active ingredient is 2-tertiarybutyl-4-cyclohexylphenyl nicotinate, or a pharmaceutically-acceptable acid addition salt thereof.

*25. A compound selected from the group consisting of cyclododecylphenyl-nicotinate, 5,6,7,8-tetrahydro-1-naphthyl-nicotinate, (1-adamantylphenyl)-nicotinate, (cyclohexylacetyl)-phenylnicotinate, 2-tertiarybutyl-4-cyclohexylphenyl nicotinate, and pharmaceutically-acceptable acid addition salts thereof.*

*26. A pharmaceutical composition useful for the treatment of hyperlipidemia comprising an effective hyperlipidemic dosage of a compound according to claim 25 in admixture together with a pharmaceutically-acceptable carrier or diluent.*

*27. Method for the treatment of hyperlipidemia comprising the step of administering to a subject in need of such therapy, by the oral or parenteral route, an effective hyperlipidemic amount of a compound selected from the group consisting of cyclododecylphenyl-nicotinate, 5,6,7,8-tetrahydro-1-naphthyl-nicotinate, (1-adamantylphenyl)-nicotinate, (cyclohexylacetyl)-phenylnicotinate, 2-tertiarybutyl-4-cyclohexylphenyl nicotinate, and pharmaceutically-acceptable acid addition salts thereof.*

* * * * *

UNITED STATES PATENT AND TRADEMARK OFFICE

CERTIFICATE OF CORRECTION

PATENT NO. : Re. 32,581

DATED : January 19, 1988

INVENTOR(S) : Arthur Scherm, Dezsoe Peteri and Klaus Hummel

It is certified that error appears in the above-identified patent and that said Letters Patent is hereby corrected as shown below:

Title Page [30] Foreign Application Priority Data, line 2 (right-hand column); "Feb. 8, 1979 [DE] Fed. Rep. of Germany . . . . . 3009099"
should read
-- Mar. 10, 1980 [DE] Fed. Rep. of Germany . . . . . 3009099 --

Col. 3, line 16; "nitocinate" should read -- nicotinate --

Col. 6, approximately line 22 (Table 2, last line); "chloro phenoxy)-" should read -- chloro-phenoxy) --

Col. 7, line 19; "e.g," should read -- e.g., --

Signed and Sealed this

Ninth Day of August, 1988

*Attest:*

*Attesting Officer*

DONALD J. QUIGG

*Commissioner of Patents and Trademarks*